United States Patent
Hwang et al.

(10) Patent No.: US 6,383,139 B1
(45) Date of Patent: *May 7, 2002

(54) ULTRASONIC SIGNAL PROCESSOR FOR POWER DOPPLER IMAGING IN A HAND HELD ULTRASONIC DIAGNOSTIC INSTRUMENT

(75) Inventors: Juin-Jet Hwang, Bothell; Lauren S. Pflugrath, Seattle; Ramachandra Pailoor, Woodinville; Terrence R. Doherty, Snohomish; Geoffrey Hugh Jones, Seattle, all of WA (US)

(73) Assignee: SonoSite, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/426,088

(22) Filed: Oct. 22, 1999

Related U.S. Application Data

(63) Continuation-in-part of application No. 09/167,964, filed on Oct. 6, 1998, now Pat. No. 6,135,961, and a continuation-in-part of application No. 08/863,937, filed on May 27, 1997, now Pat. No. 5,817,024, and a continuation-in-part of application No. 08/826,543, filed on Apr. 3, 1997, now Pat. No. 5,893,363, and a continuation-in-part of application No. 08/672,782, filed on Jun. 28, 1996, now Pat. No. 5,722,412.

(51) Int. Cl.$^7$ ................................................ A61B 8/00
(52) U.S. Cl. ........................ 600/441; 600/446; 600/447
(58) Field of Search ........................ 600/437, 440–443, 600/447, 454–456, 446; 367/7, 11, 130, 138; 73/625, 626; 382/131, 181; 395/127

(56) References Cited

U.S. PATENT DOCUMENTS

| | | | |
|---|---|---|---|
| 4,154,113 A | 5/1979 | Engeler | 73/626 |
| 5,156,152 A | 10/1992 | Yamazaki et al. | 128/661.08 |
| 5,163,434 A | 11/1992 | Kumazawa | 128/661.09 |
| 5,414,803 A * | 5/1995 | Malzbender | 395/127 |
| 5,551,434 A | 9/1996 | Iinuma | 128/661.09 |
| 5,623,930 A | 4/1997 | Wright et al. | 128/661.1 |
| 5,642,732 A | 7/1997 | Wang | 128/661.07 |
| 5,724,974 A | 3/1998 | Goodsell, Jr. et al. | 128/661.09 |
| 5,732,705 A | 3/1998 | Yokoyama et al. | 128/660.07 |
| 5,769,079 A | 6/1998 | Hossack | 128/661.08 |
| 5,785,655 A | 7/1998 | Goodsell et al. | 600/441 |
| 5,846,202 A | 12/1998 | Ramamurthy et al. | 600/450 |
| 5,860,931 A | 1/1999 | Chandler | 600/458 |
| 5,891,037 A | 4/1999 | Hossack et al. | 600/453 |
| 6,135,961 A * | 10/2000 | Pflugrath et al. | 600/447 |

* cited by examiner

Primary Examiner—Marvin M. Lateef
Assistant Examiner—Ali M Imam
(74) Attorney, Agent, or Firm—Townsend and Townsend and Crew LLP; Henry K. Woodward

(57) ABSTRACT

A hand held ultrasonic instrument is provided in a portable unit which performs both B mode and Doppler imaging. The instrument includes a transducer array mounted in a hand-held enclosure, with an integrated circuit transceiver connected to the elements of the array for the reception of echo signals. A digital signal processing circuit performs both B mode and Doppler signal processing such as filtering including wall filtering matrix and Hartley transform matrix functions, detection and Doppler estimation, as well as advanced functions such as assembly of multiple zone focused scanlines, synthetic aperture formation, depth dependent filtering, speckle reduction, flash suppression, and frame averaging. The advent of color flow imaging based on Doppler frequency estimation in medical ultrasound addresses a need for rapid assessment of overall flow characteristics in cardiac care. Typical prior art implementation utilize a high degree of temporal filtering in order to enhance the flow signal, but makes the image slow to respond to changes in flow. This is true of both directional and non-directional implementations, and is necessitated by the instability of traditional estimation techniques that are derived from older color flow techniques. A significant advantage of the present invention is excellent stability of both power and direction estimates.

47 Claims, 10 Drawing Sheets

| SWITCH FUNCTION | | DESCRIPTION | NUMBER OF CONTACTS |
|---|---|---|---|
| POWER OFF/ON | ⊂⊃ | SLIDE SWITCH | 1 |
| ACTIVE SCAN/FREEZE | ⊂⊃ | PUSH AND HOLD FOR ACTIVE SCAN | 1 |
| CPA | ○ | ENABLES AND DISABLES COLOR POWER ANGIO CPA | 1 |
| DOPPLER/CPA FILTER | ○ | HIGH/MEDIUM/LOW BUTTON CYCLES THROUGH 3 SELECTIONS | 1 |
| 3D IMAGING | ○ | ENABLES 3D CAPTURE WHEN ENGAGED BEFORE THE ACTIVE SCAN BUTTON IS PUSHED | 1 |
| PRINT | ○ | SENDS SERIAL SIGNAL TO PRINTER | 1 |
| CURSOR POSITION | ✛ | X/Y POSITION OF CURSOR | 4 |
| ENTER | ○ | ENTERS SELECTION | 1 |
| MENU | ○ | TOGGLES MENU FUNCTIONS OFF AND ON, USES CURSOR AND ENTER. FUNCTIONS: APPLICATION SELECTION USED TO ENTER ALPHA NUMERIC DATA, PATIENT ID PATIENT NAME, CINE 2D AND 3D REVIEW | 1 |
| MEASURE | ○ | ENABLES MEASUREMENTS, USES CURSOR AND ENTER | 1 |
| FOCUS | ○ | ENABLES FOCUS MODE, CURSOR UP DOWN POSITIONS FOCUS, CURSOR LEFT RIGHT SELECTS NUMBER OF ZONES | 1 |
| IMAGE | ⊙⊙ | ALLOWS THE USER TO SELECT THROUGH SEVERAL GRAY SCALE CURVES, SPATIAL AND TEMPORAL FILTERS WITH IN A PREDETERMINED SET OF SETUPS FOR A SELECTED APPLICATION | 2 |
| DEPTH | ⊙⊙ | UP/DOWN, 5 DEPTH SELECTIONS | 2 |
| TGC GAIN | ⊙⊙ | UP/DOWN | 2 |
| BRIGHTNESS | ⊙⊙ | LCD DISPLAY CONTROL UP/DOWN | 2 |
| CONTRAST | ⊙⊙ | LCD DISPLAY CONTROL UP/DOWN | 2 |

*FIG. 8*

ULTRASONIC SIGNAL PROCESSOR FOR POWER DOPPLER IMAGING IN A HAND HELD ULTRASONIC DIAGNOSTIC INSTRUMENT

BACKGROUND OF THE INVENTION

This application is a continuation-in-part of, and claims the benefit of priority from application Ser. Nos. 09/167,964 filed Oct. 6, 1998, U.S. Pat. No. 6,135,961, 08/863,937, filed on May 27, 1997, U.S. Pat. No. 5,817,024, 08/826,543, filed on Apr. 3, 1997, U.S. Pat. No. 5,893,363, and 08/672,782 filed Jun. 28, 1996, U.S. Pat. No. 5,722,412 the full disclosures of which are incorporated herein by reference.

This invention relates to medical ultrasonic diagnostic systems, and, in particular, to a fully integrated hand-held ultrasonic diagnostic instrument.

As is well known, modem ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., assignee of the present invention, were smaller, desktop units about the size of a personal computer. However, such instruments lacked many of the advanced features of today's premium ultrasound systems such as color Doppler imaging and three dimensional display capabilities. As ultrasound systems, have become more sophisticated they have also become bulkier.

However, with the ever increasing density of digital electronics, it is now possible to foresee a time when ultrasound systems will be able to be miniaturized to a size even smaller than their much earlier ancestors. The physician is accustomed to working with a hand-held ultrasonic scanhead which is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

SUMMARY OF THE INVENTION

In accordance with the principles of the present invention, a diagnostic ultrasound instrument is provided which exhibits many of the features of a premium ultrasound system in a hand-held unit. These premium system features are afforded by a digital signal processor capable of performing both greyscale and Doppler signal processing including their associated filtering, compression, flash suppression and mapping functions, as well as advanced features such as synthetic aperture formation, multiple focal zone imaging, frame averaging, depth dependent filtering, and speckle reduction. In particular, the processor provides power Doppler imaging data through use of Hartley transformation and wall filtering to calculate the Fourier power spectrum. In preferred embodiments the digital signal processor is formed on a single integrated circuit chip. This sophisticated ultrasound instrument can be manufactured as a hand-held unit weighing less than five pounds.

A new signal processing algorithm and architecture for Directional Doppler Power Imaging is presented with this invention. This algorithm is based on a concept of transforming the Doppler data after wall-filtering into the Hartley domain. Since Hartley transformation can be embedded in the wall-filtering process, Doppler power of the forward and the reverse flow components can be computed with very little processing overhead. Excluding the computation required for wall-filtering, for an ensemble of N echoes in Doppler sensing, Directional Doppler power can be computed with 2N MULTIPLIES and 4N+1 ADDS operations per pixel that is much more efficient than any existing methods. As a comparison, 6N-4 MULTIPLIES AND 4N-5 ADDS operations are required per pixel if autocorrelation method is used. To appreciate the processing efficiency, it is noted that 2N MULTIPLIES and 2N-1 ADDS operations are required per pixel to calculate the Doppler power alone. Due to simplicity of signal processing, the implementation is very low cost and is suitable for low-power VLSI implementation in a handheld ultrasound imaging system.

The invention has particular applicability in cardiac applications since flow direction and power can be computed simultaneously, rather than separately as in conventional directional power doppler. Direction of flow is obtained directly by integration of the power spectrum below and above the transmitted ultrasound frequency. This allows the imaging of regurgitant flow in the heart valve due to leaks. The imaging can be trans thoracic, trans esophagus, or by catheter to the heart. Because of the speed of the new processing algorithm, imaging limited to the cardiac cycle is feasible and practical.

The invention and objects and features thereof will be more readily apparent from the following description and appended claims when taken with the drawings.

BRIEF DESCRIPTION OF THE DRAWINGS

FIG. 8 is a chart of the user controls of the ultrasound system of FIG. 1.

DETAILED DESCRIPTION OF PREFERRED EMBODIMENTS

Figure 1:
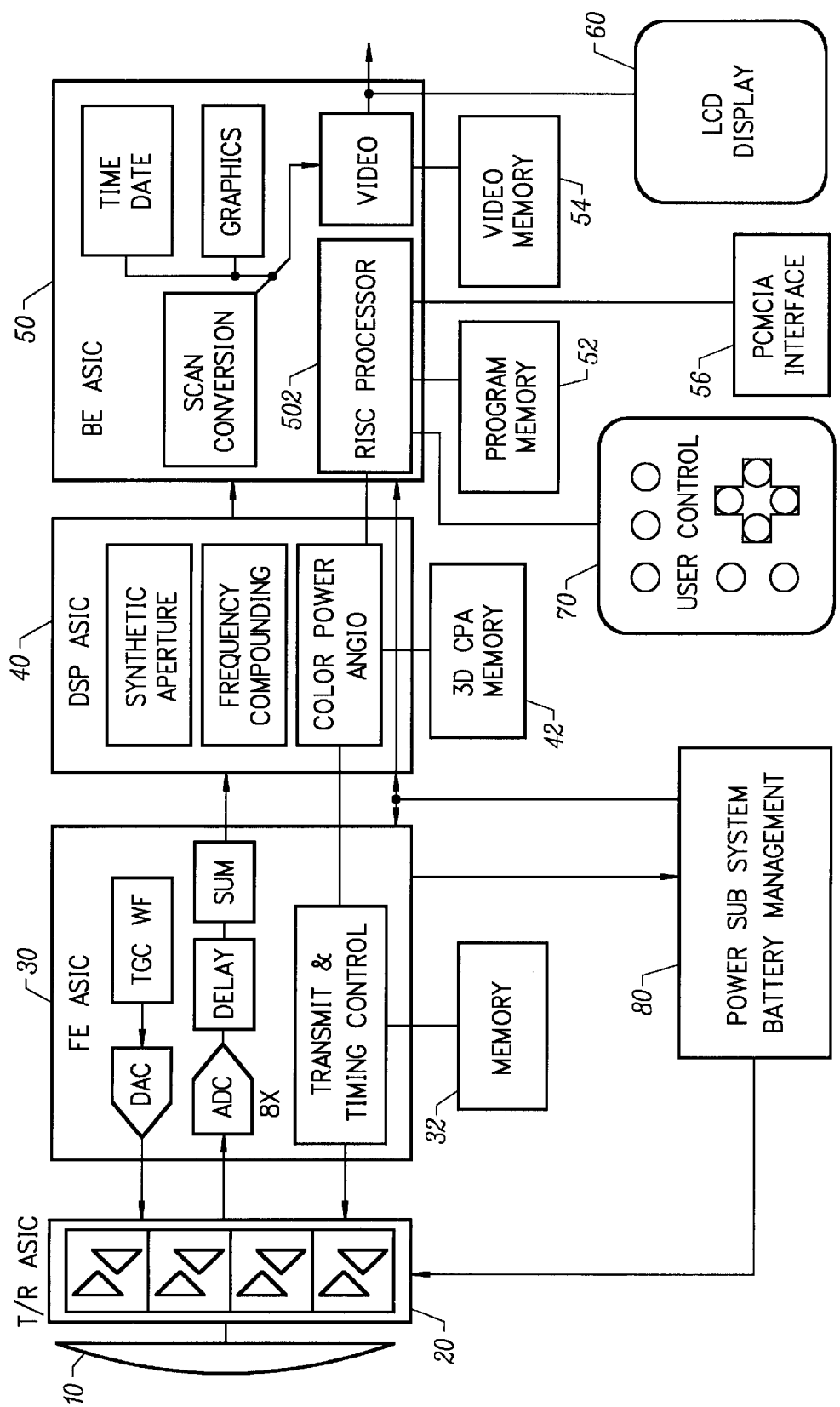
FIG. 1 illustrates in block diagram form the architecture of a hand-held ultrasound system of the present invention.

Referring first to FIG. 1, the architecture of a hand-held ultrasound system of the present invention is shown. It is possible to package an entire ultrasound system in a-single hand-held unit only through judicious selection of functions and features and efficient use of integrated circuit and ultrasound technology. A transducer array 10 is used for its solid state, electronic control capabilities, variable aperture, image performance and reliability. Either a flat or curved linear array can be used. In a preferred embodiment the array is a curved array, which affords a broad sector scanning field. While the preferred embodiment provides sufficient delay capability to both steer and focus a flat array such as a phased array, the geometric curvature of the curved array reduces the steering delay requirements on the beamformer. The elements of the array are connected to a transmit/receive ASIC 20 which drives the transducer elements and receives echoes received by the elements. The transmit/receive ASIC 20 also controls the active transmit and receive apertures of the array 10 and the gain of the received echo signals. The transmit/receive ASIC is preferably located within inches of the transducer elements, preferably in the same enclosure, and just behind the transducer. A preferred embodiment of the transmit/receive ASIC is described in detail in U.S. patent application Ser. No. 08/826,543 filed Apr. 3, 1997 and entitled ULTRASONIC ARRAY TRANSDUCER TRANSCEIVER FOR A HAND HELD ULTRASONIC DIAGNOSTIC INSTRUMENT, now U.S. Pat. No. 5,893,363.

Echoes received by the transmit/receive ASIC 20 are provided to the adjacent front end ASIC 30, which beamforms the echoes from the individual transducer elements into coherent scanline signals. The front end ASIC 30 also controls the transmit waveform timing, aperture and focusing of the ultrasound beam through control signals provided for the transmit/receive ASIC. In the illustrated embodiment the front end ASIC 30 provides timing signals for the other ASICs and time gain control. A power and battery management subsystem 80 monitors and controls the power applied to the transducer array, thereby controlling the acoustic energy which is applied to the patient and minimizing power consumption of the unit. A memory device 32 is connected to the front end ASIC 30, which stores data used by the beamformer. A preferred embodiment of the front end ASIC is described in detail in U.S. patent application Ser. No. 08/863,937 filed May 27, 1997 and entitled HAND HELD ULTRASONIC DIAGNOSTIC INSTRUMENT WITH DIGITAL BEAMFORMER, now U.S. Pat. No. 5,817,024.

Beamformed scanline signals are coupled from the front end ASIC 30 to the digital signal processing ASIC 40. The digital signal processing ASIC 40 filters the scanline signals, processes them as B mode signals, Doppler signals, or both, and in the preferred embodiment also provides several advanced features including synthetic aperture formation, frequency compounding, Doppler processing such as power Doppler (color power angio) processing, and speckle reduction as more fully detailed below.

The ultrasound B mode and Doppler information is then coupled to the adjacent back end ASIC 50 for scan conversion and the production of the video output signals. A memory device 42 is coupled to the back end ASIC 50 to provide storage used in three dimensional power Doppler (3D CPA) imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in live Cineloop® realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set controller) processor 502. The RISC processor is coupled to the front end and digital signal processing ASICs to control and synchronize the processing and control functions throughout the hand-held unit. A program memory 52 is coupled to the back end ASIC 50 to store program data which is used by the RISC processor to operate and control the unit. The back end ASIC 50 is also coupled to a data port configured as an intrared transmitter or a PCMCIA interface 56. This interface allows other modules and functions to be attached to or communicate with the hand-held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand-held ultrasound system.

Power for the hand-held ultrasound system in a preferred embodiment is provided by a rechargeable battery. Battery power is conserved and applied to the components of the unit from the power subsystem 80. The power subsystem 80 includes a DC converter to convert the low battery voltage to a higher voltage which is applied to the transmit/receive ASIC 20 to drive the elements of the transducer array 10.

Figure 2B:
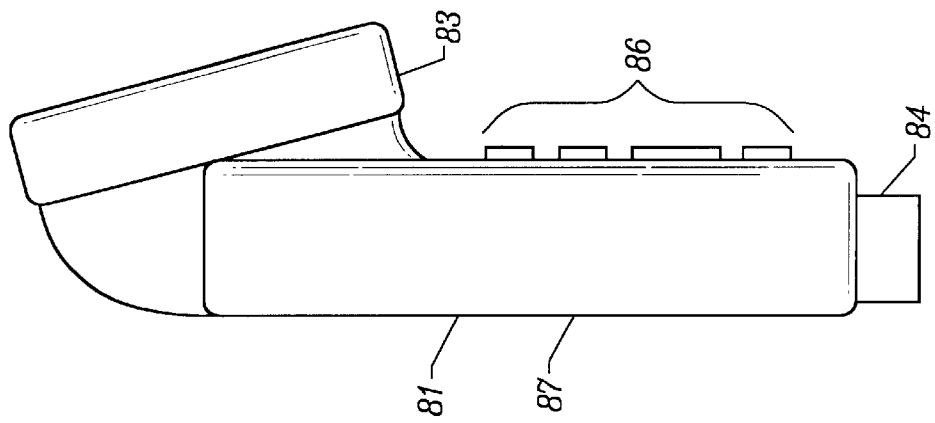
FIGS. 2a and 2b are front and side views of a hand-held ultrasound system of the present invention which is packaged as a single unit.
Figure 2A:
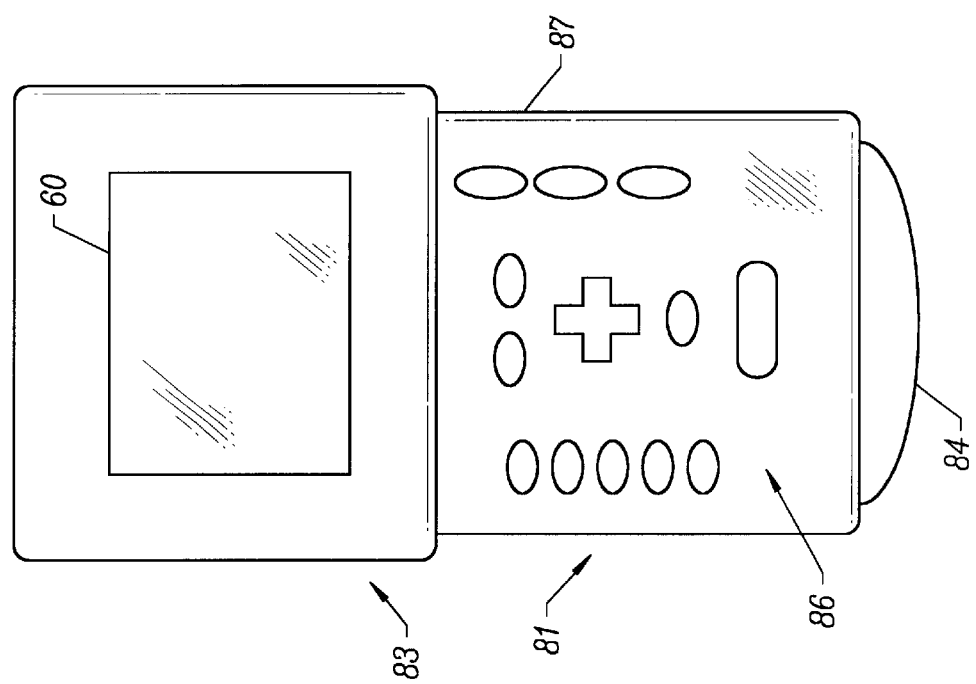

FIGS. 2*a* and 2*b* illustrate a one piece unit 87 for housing the ultrasound system of FIG. 1. The front of the unit is shown in FIG. 2*a*, including an upper section 83 which includes the LCD display 60. The lower section 81 includes the user controls as indicated at 86. The user controls enable the user to turn the unit on and off, select operating characteristics such as the mode (B mode or Doppler), color Doppler sector or frame rate, and special functions such as three dimensional display. The user controls also enable entry of time, date, and patient data. A four way control, shown as a cross, operates as a joystick to maneuver cursors on the screen or select functions from a user menu. Alternatively, a mouse ball or track pad can be used to provide cursor and other controls in multiple directions. Several buttons and switches of the controls are dedicated for specific functions such as freezing an image and storing and replaying an image sequence from the Cineloop memory.

At the bottom of the unit 87 is the aperture 84 of the curved transducer array 10. In use, the transducer aperture is held against the patient to scan the patient and the ultrasound image is displayed on the LCD display 60.

FIG. 2*b* is a side view of the unit 87, showing the depth of the unit. The unit is approximately 20.3 cm high, 11.4 cm wide, and 4.5 cm deep. This unit contains all of the elements of a fully operational ultrasound system with a curved array transducer probe, in a single package weighing less than five pounds. A major portion of this weight is attributable to the battery housed inside the unit.

Figure 4:
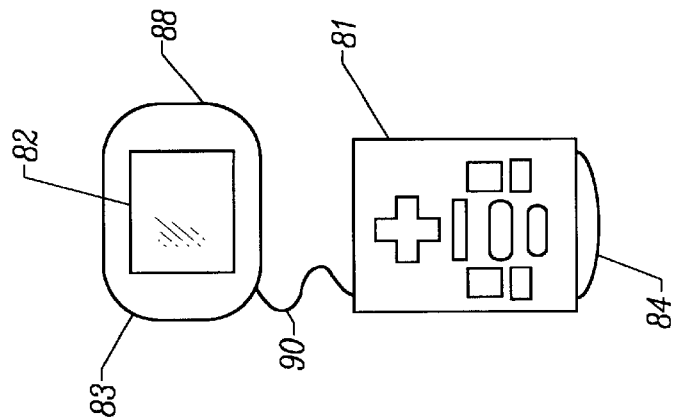
FIG. 4 illustrates the two units of a hand-held ultrasound system of the present invention in a two-unit package.
Figure 3B:
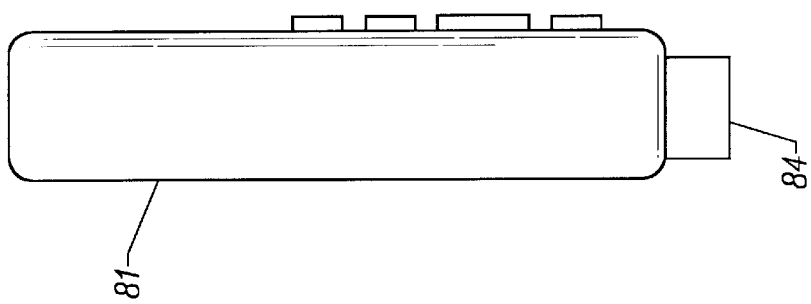
FIGS. 3a and 3b are front and side views of the transducer unit of a two-unit hand-held ultrasound system of the present invention.
Figure 3A:
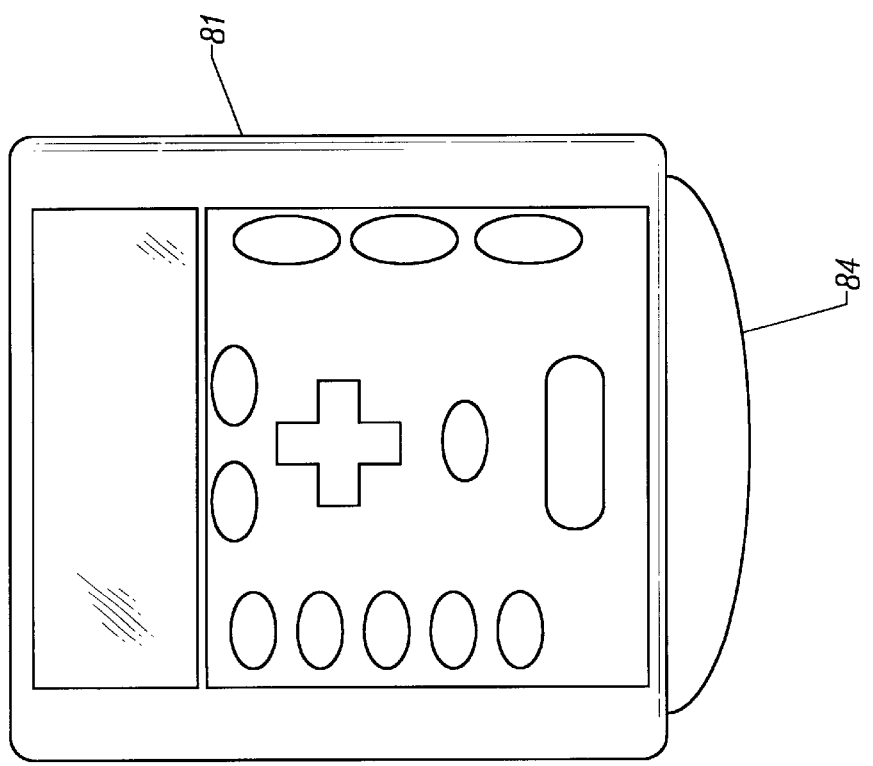

FIGS. 3 and 4 illustrate a second packaging configuration in which the ultrasound system is housed in two separate sections. A lower section 81 includes the transducer array, the electronics through to a video signal output, and the user controls. This lower section is shown in FIG. 3*a*, with the curved transducer array aperture visible at the bottom. The lower section is shown in the side view of FIG. 3*b*. This lower section measures about 11.4 cm high by 9.8 cm wide by 2.5 cm deep. This unit has approximately the same weight as a conventional ultrasound scanhead. This lower section is connected to an upper section 83 as shown in FIG. 4 by a cable 90. The upper section 83 includes an LCD display 82 and a battery pack 88. The cable 90 couples video signals from the lower unit 81 to the upper unit for display, and provides power for the lower unit from the battery pack 88. This two part unit is advantageous because the user can maneuver the lower unit and the transducer 84 over the patient in the manner of a conventional scanhead, while holding the upper unit in a convenient stationary position for viewing. By locating the battery pack in the upper unit, the lower unit is lightened and easily maneuverable over the body of the patient.

Other system packaging configurations will be readily apparent. For instance, the front end ASIC 30, the digital signal processing ASIC 40, and the back end ASIC 50 could be located in a common enclosure, with the beamformer of the front end ASIC connectable to different array tranducers. This would enable different transducers to be used with the digital beamformer, digital filter, and image processor for different diagnostic imaging procedures. A display could be located in the same enclosure as the three ASICs, or the output of the back end ASIC could be connected to a separate display device. Alternatively, the transducer array 10, transmit/receive ASIC 20 and front end ASIC 30 could be in the transducer enclosure and the balance of the system in the battery and display unit. The configuration of FIG. 4 could be changed to relocate the user controls onto the display and battery pack unit, with the ultrasound ASICs located in the unit with the transducer array.

Figure 5:
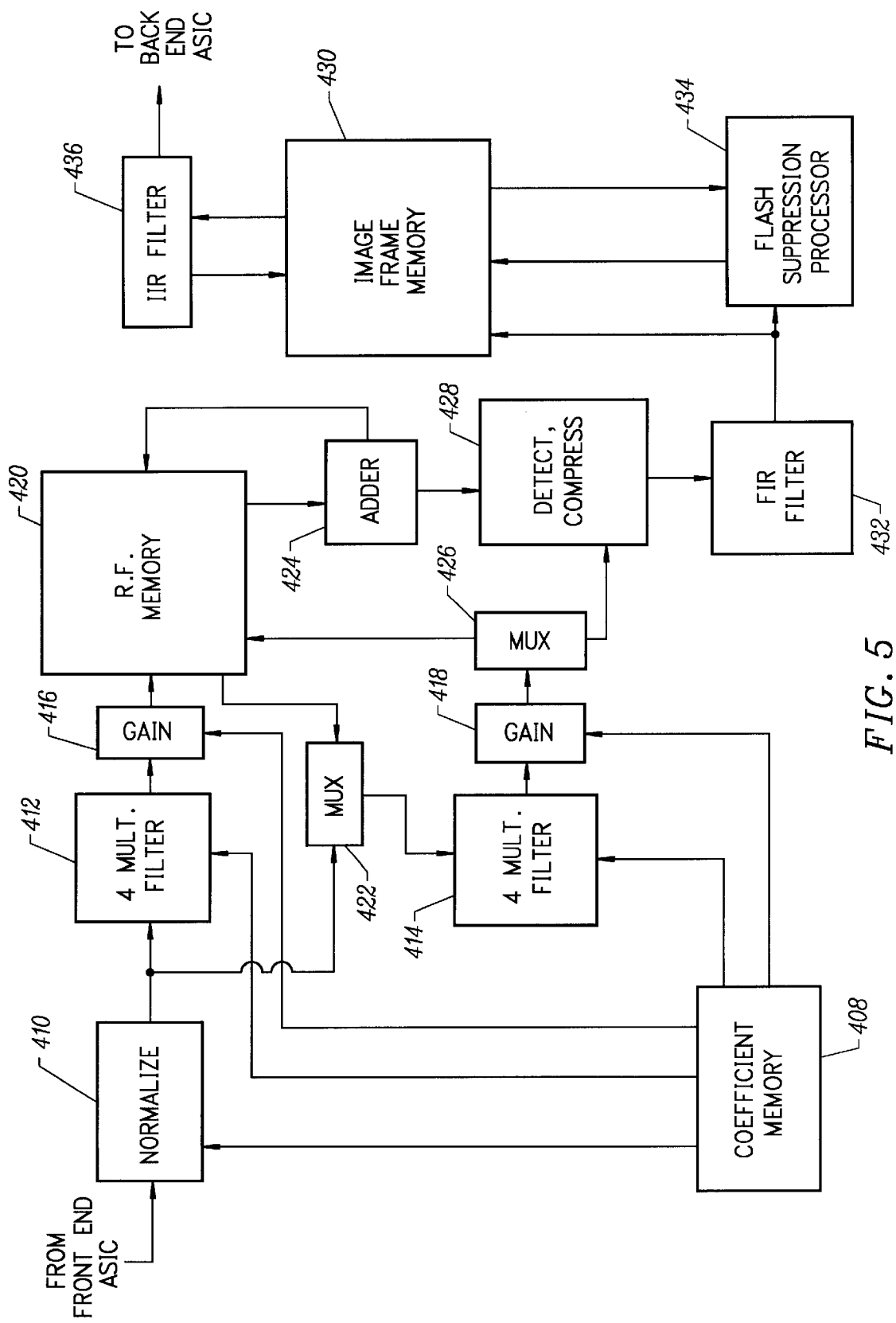
FIG. 5 is a block diagram of the digital signal processing ASIC of the ultrasound system of FIG. 1.

Referring to FIG. 5, a detailed block diagram of the digital signal processing ASIC 40 is shown. Scanline signals from the front end ASIC 30 are received by a normalization circuit 410, where they are multiplied by a variable coefficient supplied by coefficient memory 408 to normalize the received signals for aperture variation. When the transducer is receiving signals along the scanline from shallow depths, a relatively small aperture, such as four or eight transducer elements, is used to receive echo signals. As the reception depth along the scanline increases, the aperture is incrementally increased so that the full 32 element aperture is used at maximum depths. The normalization circuit 410 will multiply the received scanline signals by appropriate coefficients over the range of aperture variation, such as factors of four or eight, to normalize the signals for this aperture variation effect.

Figure 6:
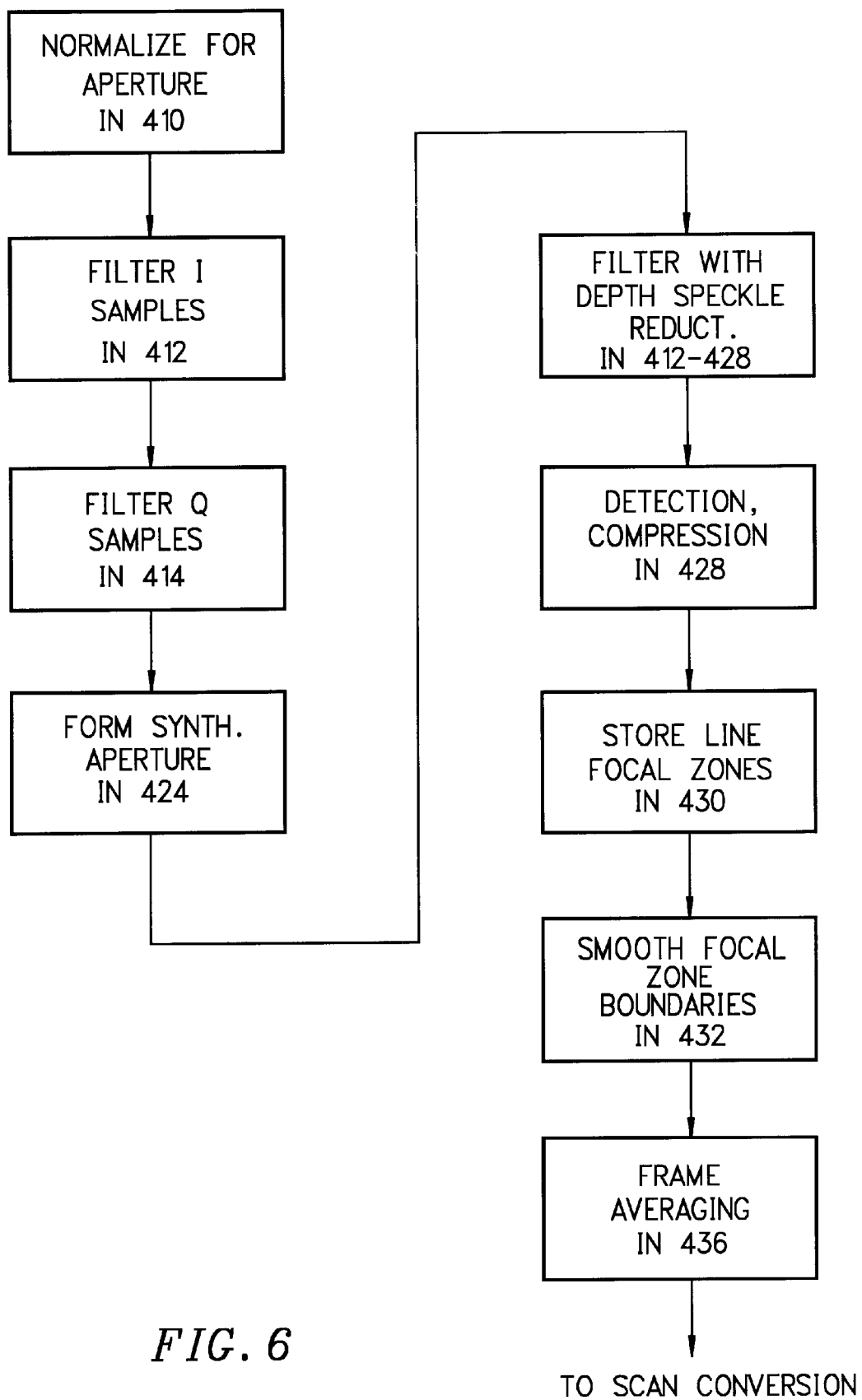
FIG. 6 is a flowchart of B mode processing by the digital signal processing ASIC.

When the ultrasound system is operated in the B mode to form a structural image of tissue and organs, the digital signal processor is operated as shown by the flowchart of FIG. 6. The normalized echo signals follow two paths in FIG. 5, one of which is coupled to a four multiplier filter 412 and the other of which is coupled by a multiplexer 422 to a second four multiplier filter 414. Each multiplier filter includes a multiplier and an accumulator which operate as an FIR (finite impulse response) filter. Scanline echo signals are shifted sequentially into a multiplier, multiplied by coefficients supplied by the coefficient memory 408, and the products are accumulated in the accumulator at the output of the multiplier. The coefficients for the filter 412 are chosen to multiply the echo signals by a cosine function and the coefficients for the filter 414 are chosen to multiply the echo signals by a sine function, preparatory for I and Q quadrature signal detection. The four multiplier filters produce accumulated signals at a rate which is less than the input rate to the multipliers, thereby performing decimation band pass filtering. When the signal bandwidth exceeds the display bandwidth of the display monitor, the image lines will flicker due to an aliasing condition. The decimation filtering is designed to reduce the signal bandwidth as well as the data rate to match the display bandwidth of the monitor. By applying a succession of input signals and coefficients to a multiplier and accumulating intermediate products, the effective length of the filter can be increased. For instance, input signals 1–8 can be sequentially weighted by the fourth multiplier and the products accumulated in the fourth accumulator; input signals 3–10 can be weighted by the third multiplier and the products accumulated in the third accumulator; input signals 5–12 can be weighted by the second multiplier and the products accumulated in the second accumulator; and the input signals 7–14 can be weighted by the first multiplier and the products accumulated in the first accumulator. The data rate has thereby been decimated by two, and each multiplier and accumulator is effectively operated as an eight tap filter. Thus, it is seen that the effective number of taps of the filter is a product of the number of multipliers (four in this example) and the decimation rate (two in this example).

Additionally, this filter reduces r.f. noise and quantization noise through its bandwidth limiting effects. I and Q echo signal samples are produced at the outputs of filters 412 and 414, amplified if desired by the multipliers of gain stages 416 and 418, then stored in the r.f. memory 420. The Q samples are coupled to the r.f. memory by a multiplexer 426.

When a synthetic aperture image is to be formed, partially summed scanlines from a portion of the full aperture are acquired following separate pulse transmissions, then combined to form full aperture scanlines. When the synthetic aperture is formed from two pulse transmissions, the I and Q samples from the scanline of the first half of the aperture are stored in the r.f. memory 420 until the I and Q samples from the other half of the aperture are received. As the samples from the second half of the aperture are received, they are combined with their spatially corresponding counterparts by an adder 424. The size of the r.f. memory is kept to a minimum by storing the aperture signals after decimation filtering, which reduces the size of the memory required to store the scanline signal samples.

After the I and Q samples for the full aperture have been formed, the echo samples are coupled from the adder 424 to a detection and compression circuit 428. This circuit includes two shift registers and a multiplier arranged to form a CORDIC processor for performing envelope detection of the form $(I^2+Q^2)^{1/2}$. See, for instance, "The CORDIC Trigonometric Computing Technique, by J. E. Volder, *IRE Trans. on Elect. Computers,* (September 1959). The detected signal is compressed and scaled to map the detected signals to a desired range of display gray levels.

Following detection and compression mapping, the grayscale signals are lowpass filtered in an FIR filter 432, then stored in an image frame memory 430. If the selected scanning mode utilizes a single transmit focal point, the grayscale signals are transmitted to the back end ASIC 50 for scan conversion. Prior to leaving the ASIC 40, the grayscale signals can be frame averaged by an infinite impulse response (IIR) filter 436 which utilizes image frame memory 430 as a frame buffer and incorporates one multiplier and two adders to perform frame to frame averaging of the form $$F_{out}=(1-\alpha)F_{out-1}+\alpha F_{new}=F_{out-1}+\alpha(F_{new}-F_{out-1})$$

where the multiplier coefficient is $\alpha$. If the coefficient is a binary number (e.g., 0.5, 0.25, 0.125) $F_{out}$ can be obtained with an add-shift-add operation.

If multiple focal zones are used, each received scanline segment is stored in the r.f. memory 420 until scanline segments from the entire display depth have been received.

Preferably the scanline segments for one complete focal zone are acquired before transmitting and receiving segments from another focal zone. When all segments for a scanline have been acquired, each complete scanline is then read out of the r.f. memory and filtered by the FIR filter 432, which smoothes the boundaries between the segments for a more pleasing, artifact-free image.

If both multiple zone focusing and synthetic aperture are used, the scanline segments of both halves of the aperture are received over the full focal zone and assembled in the r.f. memory 420. Corresponding scanline segments are then received from other focal zones and joined with the segments from the first received focal zone. The completed scanlines are then filtered by FIR filter 432 to smooth the boundaries between segments.

The user may choose to process the grayscale image with certain image enhancement features, such as depth dependent filtering or speckle reduction such as the frequency compounding technique described in U.S. Pat. No. 4,561,019. These optional processing techniques necessitate the use of the filters 412 and 414 for separate bandpass filtering of the scanline signals and absolute value detection rather than quadrature detection. In the case of depth dependent filtering the received echo signals are multiplied by cosine functions in both of filters 412 and 414, but with coefficients chosen so that one filter produces output signals in a high passband and the other produces output signals in a low passband. The output signals produced by the two filters are of the form $I_1=h_1(t)\cos\omega_H t$ and $I_2=h_2(t)\cos\omega_L t$. These two output signals are amplified in gain stages 416 and 418 by complementary time varying gain control functions. The high frequency passband signals $I_1$ are initially amplified strongly, then the gain is decreased as echo signals are received from increasing depths along the scanline. In a complementary manner the low frequency passband signals $I_2$ are initially at a low level, then amplified in an increasing manner with depth as the high frequency gain is rolled off. Thus, signals at shallow depths will exhibit a relatively high passband, and signals from greater depths will pass through a relatively lower passband which reduces high frequency noise at the greater depths. Detection in the CORDIC processor of circuit 428 is performed by absolute value detection by squaring $I_1$ and $I_2$, then summing the results. Following summation, the signals are log compressed to the desired grayscale mapping characteristic. Alternatively, the signals passed by the separate passbands are summed by the adder 424, then detected by absolute value detection in the detection and compression circuitry 428 and mapped.

The same processors can be used to provide speckle reduction by frequency compounding. The coefficients of one of the filters 412, 414 are chosen to filter the received signals by a high frequency passband, and the coefficients of the other filter are chosen to filter the received signals by a contiguous low frequency passband. The coefficients of the gain stages 416, 418 are chosen to equalize the responses of the two passbands. The signals of the high and low passbands are coupled to the detection and compression circuitry where the passbands are separately detected through absolute value detection as described above, then the detected signals are log compressed to the desired grayscale mapping characteristic and summed on a spatial basis.

Figure 7:
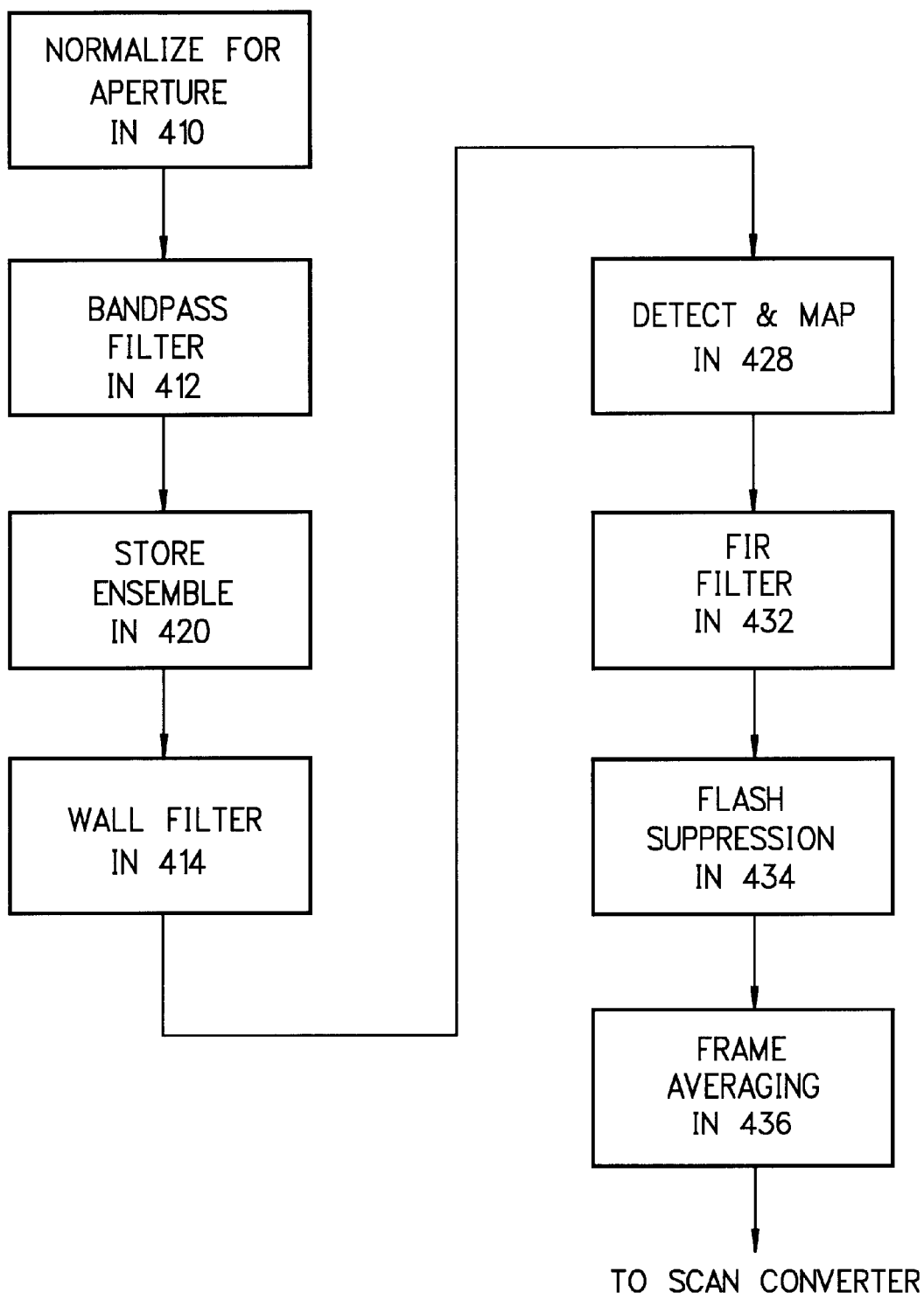
FIG. 7 is a flowchart of Doppler processing by the digital signal processing ASIC.

The processing of Doppler echo signals for power Doppler (CPA) display is shown in FIG. 5 together with the flowchart of FIG. 7. Each scanline vector is scanned repetitively, for instance eight times, to assemble an ensemble of Doppler information along the vector. Each received scanline of echo signals is normalized by the normalization circuit 410 and undergoes decimation band pass filtering in the filter 412. Each scanline of the ensemble is stored in the r.f. memory 420 until a complete ensemble has been accumulated. The scanlines of each ensemble are coupled by the multiplexer 422 to the four multiplier filter 414, which performs wall filtering and Doppler power estimation through matrix filtering. Wall filtering is performed by selection of appropriate multiplier coefficients and the matrix filtering is of the form $$\begin{bmatrix} Y_1 \\ Y_2 \\ Y_3 \\ \vdots \\ Y_n \end{bmatrix} = \begin{bmatrix} a_{11} & a_{12} & a_{13} & \cdots & a_{1n} \\ b_{11} & b_{12} & b_{13} & \cdots & b_{1n} \\ c_{11} & c_{12} & c_{13} & \cdots & c_{1n} \\ \vdots & \vdots & \vdots & & \vdots \\ z_{11} & z_{12} & z_{13} & \cdots & z_{1n} \end{bmatrix} \cdot \begin{bmatrix} x_1 \\ x_2 \\ x_3 \\ \vdots \\ x_n \end{bmatrix}$$

where $x_1 \ldots x_n$ are spatially aligned signals from the ensemble of scanlines and $y_1 \ldots y_n$ are output Doppler values. In a preferred embodiment a four multiplier filter is used for matrix filtering, and the filtering is performed sequentially and incrementally. Intermediate products are accumulated as described above, thereby extending the filter length. For example, in processing the above matrix with a four multiplier filter, the intermediate products $a_{11}x_1+a_{11}x_2+a_{13}x_3+a_{14}x_4$ are formed initially and summed in the accumulator. Then products $a_{15}x_5+a_{16}x_6+a_{17}x_7+a_{18}x_8$ are formed by the multipliers and summed in the accumulator with the previously computed intermediate products. By accumulating intermediate products in this manner the four multipliers and accumulator can be extended to a filter of any desired length, restricted only by the maximum processing time available. The Doppler values are coupled to the detection and compression circuitry 428 through the gain stage 418 and the multiplexer 426, where the Doppler signal amplitude at each echo location along the scanline is detected through absolute value detection of the form $$y = \sum_n^{1-n} Yn^2$$

The Doppler values y are compressed and scaled using the CORDIC processor of the detection and compression circuitry 428.

Once the Doppler signal amplitude values have been detected and filtered by FIR filter 432, the resulting values are spatially stored and image clutter is removed by a flash suppression processor 434, which eliminates large frame to frame variations in the displayed signals. Flash suppression processor 434 may operate by any of a number of known flash suppression techniques, such as frame to frame comparison and elimination or the notch filtering technique of U.S. Pat. No. 5,197,477. A preferred technique for flash suppression processing is min-max filtering as described in detail in the parent U.S. patent application Ser. No. 08/672,782.

The image frame memory 430 is capable of storing either a gray scale frame or a power Doppler frame. Each frame can be temporally filtered by the IIR filter 436, which performs frame averaging on a point-by-point basis as described above. The temporally filtered image information is then provided to the back end ASIC 50 for scan conversion and display.

The sequences of operating the digital signal processing ASIC 40 for B mode (two dimensional) echo and Doppler processing, respectively, are outlined in the flowcharts of FIGS. 6 and 7, respectively. The number in each flowchart block of FIGS. 6 and 7 refers to the numbered processor in the ASIC block diagram of FIG. 5.

The image frame memory 430 of the digital signal processing ASIC 40 shares a common architecture and implementation technology with the frame buffer memory of the back end ASIC 50. To take advantage of this commonality and the resultant efficiency in ASIC fabrication and density, the image frame memory 430 and its associated flash suppression processor 434 and IIR filter 436 can be located on the back end ASIC 50, thereby partitioning the digital signal processing ASIC and the back end ASIC at the output of FIR filter 432. Thus, the digital signal processing function of FIG. 5 up through the output of FIR filter 432, or all of the functions shown in FIG. 5 can be fabricated on a single integrated circuit chip, depending upon this partitioning choice and other integrated circuit layout considerations.

In accordance with another application of the processor, the wall filtering function of four multiplier filter 414 is used to calculate the Fourier power spectrum via Hartley Transformation. Since Hartley transform and wall filtering can be completed in a single matrix filtering process, no additional cost is incurred in Hartley transform. The Fourier power spectrum can be obtained from Hartley components with real arithmetic. Thus, spectral analysis in PW Doppler may also be processed using the same circuit with great computational savings.

The process of wall filtering, windowing, and Hartley transform on the analytic signal vector $\vec{z}$ may be represented by a concatenation of three matrix operations $\vec{z}$ is complex which consists of echoes from N pulses.

$$M\vec{z} = M_h M_w M_f \vec{z};$$

where $M_f$ is the wall filtering matrix, $M_h$ is the Hartley transformation matrix, and $M_w$ is a matrix for windowing to suppress the spectral sidelobes in the Fourier spectrum.

The matrix entries of the Hartley transformation matrix $M_h$ are $$M_h(n+1, k+1) = \frac{1}{\sqrt{N}}\left(\cos\left(\frac{2\pi nk}{N}\right) + \sin\left(\frac{2\pi nk}{N}\right)\right),$$

$$n = 0, \ldots, N-1; k = 0, \ldots, N-1.$$

The window function can be either Hamming or Hann. Let the ith filtering coefficient be w(i) and i=1, ...,N. Then matrix $M_w$ can be constructed using w(i)'s according to $$M_w = \begin{bmatrix} w(1) & 0 & \cdots & 0 & 0 \\ 0 & w(2) & \cdots & \vdots & 0 \\ \vdots & \vdots & \cdots & \vdots & \vdots \\ 0 & \vdots & \cdots & w(N-1) & 0 \\ 0 & 0 & \cdots & 0 & w(N) \end{bmatrix}$$

After wall filtering, windowing and Hartley transform, Hartley components $\check{H}$ are obtained.

$$\vec{H} = M\vec{z} = M(\vec{s} + j\vec{s}) = \vec{H}_s + j\vec{H}_s; \quad (1)$$

where $\vec{s}$ and $\vec{s}$ are the I and Q components of the signal $\vec{z}$. Notice that to obtain the Hartley components $\check{H}$, the computation required is the same as the wall filtering process. The Hartley components are obtained with no cost.

The new signal processing architecture is based on a concept of modifying the filtering coefficients in the matrix wall filtering process to obtain the Fourier power spectrum via Discrete Hartley transformation for mean frequency estimate. Since Hartley transform and wall filtering can be completed in a single matrix filtering process, no additional cost is incurred in Hartley transform. The Fourier power spectrum is obtained from the wall-filtered Hartley components with simple hardware. Not only color flow processing and color power Doppler can be supported at low cost using this approach, spectral Doppler, directional power Doppler, 2D echo processing, frequency compounding, tracking filtering, can also be supported with very little overhead.

Hardware for implementing the NxN matrix filtering process is similar to implementing the Nth order FIR filter except the filtering coefficients are changed from sample to sample. Mathematically, the filtering operation may be represented by $\vec{y} = M_f \vec{z}$, where the signal vector $\vec{z}$ is complex and the filtering matrix $M_f$ is real. Thus, no increase of computation complexity if the filtering matrix $M_f$ is replaced by a concatenation of multiple matrices, each represents an implementation of a mathematical operation on $\vec{y}$. Hartley transformation is a real transform which preserves the spectral information of the Fourier transformation. Since the Fourier components can be converted from the Hartley components based on real arithmetic, the mean Doppler power and the mean Doppler frequency shift may easily be calculated from the Fourier power spectrum with great computational savings. It is found that the amount of computation required to calculate these flow imaging parameters based on Hartley-Fourier transform implementation is less than a half of that required from autocorrelation based implementation.

Since full Fourier power spectrum is available for each sample volume, flow classification may be performed based on spectral analysis. Further improvement of wall filtering is also possible after matrix wall filtering by shaping the spectrum in frequency domain. Moreover, estimating the mean frequency from autocorrelation of unity lag is only valid when the spectrum is symmetrical. Since this is generally not true, the frequency estimate based on autocorrelation of unit lag is biased. Estimating the mean frequency based on Hartley-Fourier approach is correct for any spectral shapes. Higher order Hartley-Fourier transformation can be implemented in the matrix filtering process by augmenting the matrix filtering coefficients to gain frequency resolution. Processing architecture for both single channel processing and quadrature channel processing are also included in this report.

The time-varying wall filtering process may be represented by the following matrix operation, $$\vec{y} = M_f \vec{z} = M_f(\vec{s} + j\vec{s}) \quad (2)$$

where $\vec{z}$ is an analytic signal vector which consists of an in-phase component vector $\vec{s}$ and a quadrature component vector $\vec{s}$, $\vec{y}$ is the output signal.

In color flow imaging, the mean of the Doppler power spectrum P(f) is calculated to represent the mean velocity of the flow at a sample volume. Mathematically, the mean frequency is defined as shown in Equation (2).

$$\bar{f} = \frac{\int_{-\infty}^{\infty} fP(f)df}{\int_{-\infty}^{\infty} P(f)df} \tag{3}$$

In commercial systems, the mean frequency $\bar{f}$ is computed by detecting the phase of the autocorrelation of the signal vector $\overset{v}{y}$ with unity lag. The other approach is to estimate the mean frequency via Fourier transformation.

Discrete Fourier transformation may be implemented in matrix operation such as $$\overset{\perp}{F} = M_d \overset{r}{y} = M_d M_f \overset{r}{z} = M_d M_f \left(\overset{r}{s} + j\overset{\perp}{s}\right) = M_{ef}\left(\overset{r}{s} + j\overset{\perp}{s}\right) \tag{4}$$

where $$M_{ef} = M_d M_f \tag{5}$$

Thus, the DFT matrix $M_d$ may be concatenated with the filter matrix $M_f$ into a single matrix $M_{ef}$. Since the DFT matrix $M_d$ is complex, the computation required for calculating the Fourier magnitude spectrum by concatenating the DFT matrix $M_d$ with wall filtering matrix $M_f$ is quadruple of that required for wall filtering along, thus, is not cost effective.

Hartley transformation is a real transform which carries the spectral information of the Fourier transformation. Since the Hartley components may be converted into the Fourier component based on real arithmetic, the Fourier power spectra may be computed with great computational savings.

Let the Discrete Hartley Transformation matrix by $M_h$, the Hartley transformation of the analytic signal $\overset{v}{z}$ may be represented by $$\overset{v}{H} = M_h \overset{r}{y} = M_h M_f \overset{r}{z} = M_h M_f \left(\overset{r}{s} + j\overset{\perp}{s}\right) = M_{eh}\left(\overset{r}{s} + j\overset{\perp}{s}\right) \tag{6}$$

where $$M_{eh} = M_h M_f \tag{7}$$

Since the matrix $M_{eh}$ is real, the mathematical operation of Equation (6) is similar to that of Equation (2), thus Hartley transformation may be embedded into the wall filtering processing without additional computational cost.

Let us define $$\overset{v}{H} = \overset{\perp}{H}_s + j\overset{\perp}{H}_{\tilde{s}} = M_{eh}\overset{r}{s} + jM_{eh}\overset{\perp}{\tilde{s}} \tag{8}$$

Using Equations (A10) and (A11), the kth component of the Fourier power spectrum may be calculated as $$P_z(k) = \tag{9}$$

$$F_z(k) * F_z^*(k) = \frac{1}{2}\left[(H_{\tilde{s}}(k) + H_s(N-k))^2 + (H_s(k) - H_{\tilde{s}}(N-k))^2\right]$$

and $$P_z(0) = H_s^2(0) = H_{\tilde{s}}^2(0) \tag{10}$$

where N is the dimension of the vector that is equal to the ensemble length of Doppler sensing.

In color flow processing, the signal $\overset{v}{z}$ is filtered by the quadrature band pass filter in which the DC is suppressed, thus $P_z(0)=0$. The coefficient ½ in the power spectrum computation may be neglected with losing generality of a normalized Fourier power spectrum.

The computation required in Equation (9) is 2N additions and 2N square operations. To calculate the Doppler power at a sample volume one may calculate $$P = \sum_k P_z(k) \tag{11}$$

For mean frequency computation at a pixel $$\bar{f} = \frac{1}{P}\sum_k \lambda(k)P_z(k) \tag{12}$$

where $\lambda(k)$ is the frequency corresponding to the kth bin in the Fourier power spectrum. For peak frequency computation at a pixel $$P_{peak} = \underset{k_p}{max}(P_{k_p}) \tag{13}$$

$$f_{peak} = \lambda(k_p) \tag{14}$$

Color flow imaging based on autocorrelation method, both R(0) and the phase of R(1) must be computed. Assuming the ensemble length is N, there are 2N multiplication and N additions are required to compute R(0)=

$$R(0) = \sum_{i=1}^{i=N} I_i^2 + Q_i^2.$$

There are 4N-4 real multiplication (or N-1 complex multiplication) and 2N-2 additions to calculate R(1)=

$$R(1) = \sum_{i=1}^{i=N-1} z_i z_{i+1}^*.$$

Two multiplication and an arctangent operation required to calculate $\Phi(R(1))$. Thus, the computation required for color flow imaging based on autocorrelation is 6N—2 real multiplication, 3N—2 real additions and an arctangent operation.

For Hartley-Fourier approach, there are 2N multiplication and 2N-2 additions are required to compute the power spectrum (Equation (9). N-1 multiplication and N-2 additions for mean frequency estimate (Neglecting the DC term in Equation (10) since it is zero). Therefore, total of 3N-1 multiplication and 3N-4 additions are required for mean frequency estimate and Doppler power computation. If peak frequency is desired, 2N multiplication, 2N-2 additions and N-2 comparisons are required.

Thus, the computation complexity required for color flow imaging based on Hartley-Fourier transform implementation is less than a half of that required from the autocorrelation based implementation. Yet complete Fourier spectrum is preserved that can be used for flow classification or further improvement of wall filtering in frequency domain. Moreover, estimating the mean frequency from autocorrelation of unity lag is only valid when the spectrum is symmetrical. This is in general not true, thus, the estimate is biased. Estimating the mean frequency based on Hartley- Fourier approach is correct for any spectral shape. In implementation, since λ(k) is defined according to the dimension of the Hartley-Fourier transform, the values of λ(k)'s are fixed. Thus, the filtering coefficients of the FIR filter for mean frequency estimation are also fixed. This will greatly simplify the implementation in ASIC.

If the dimension of the vector $\overset{\perp}{y}$ in Equation (6) is augmented from N×1 to m×1 by padding zeros, the frequency resolution may be improved by a factor of m/N as a result of higher order Hartley-Fourier transformation. The higher order HF transformation may be described as $$\overset{v}{H}_{mXl} = (M_h)_{mXm} \begin{bmatrix} \overset{\perp}{y}_{NXl} \\ 0_{(m-N)Xl} \end{bmatrix} \quad (15)$$

where $$(M_{eh})_{mXm} = (M_h)_{mXm} \begin{bmatrix} M_{f,NXN} \\ 0_{(m-N)XN} \end{bmatrix} \quad (16)$$

Since the rightmost m-N entries of each row in matrix $M_{eh}$ are zero, Equation (15) may be rewritten into Equation (17)

$$\overset{v}{H}_{mXl} = (M_{eh})_{mXN} \overset{r}{z}_{NXl} \quad (17)$$

Thus, the dimension of the Matrix $M_{eh}$ is mXN, the dimensions of input signal vector $\overset{r}{z}$ and the output vector $\overset{v}{H}_{mX1}$ are NX1 and mX1 respectively.

Figure 9:
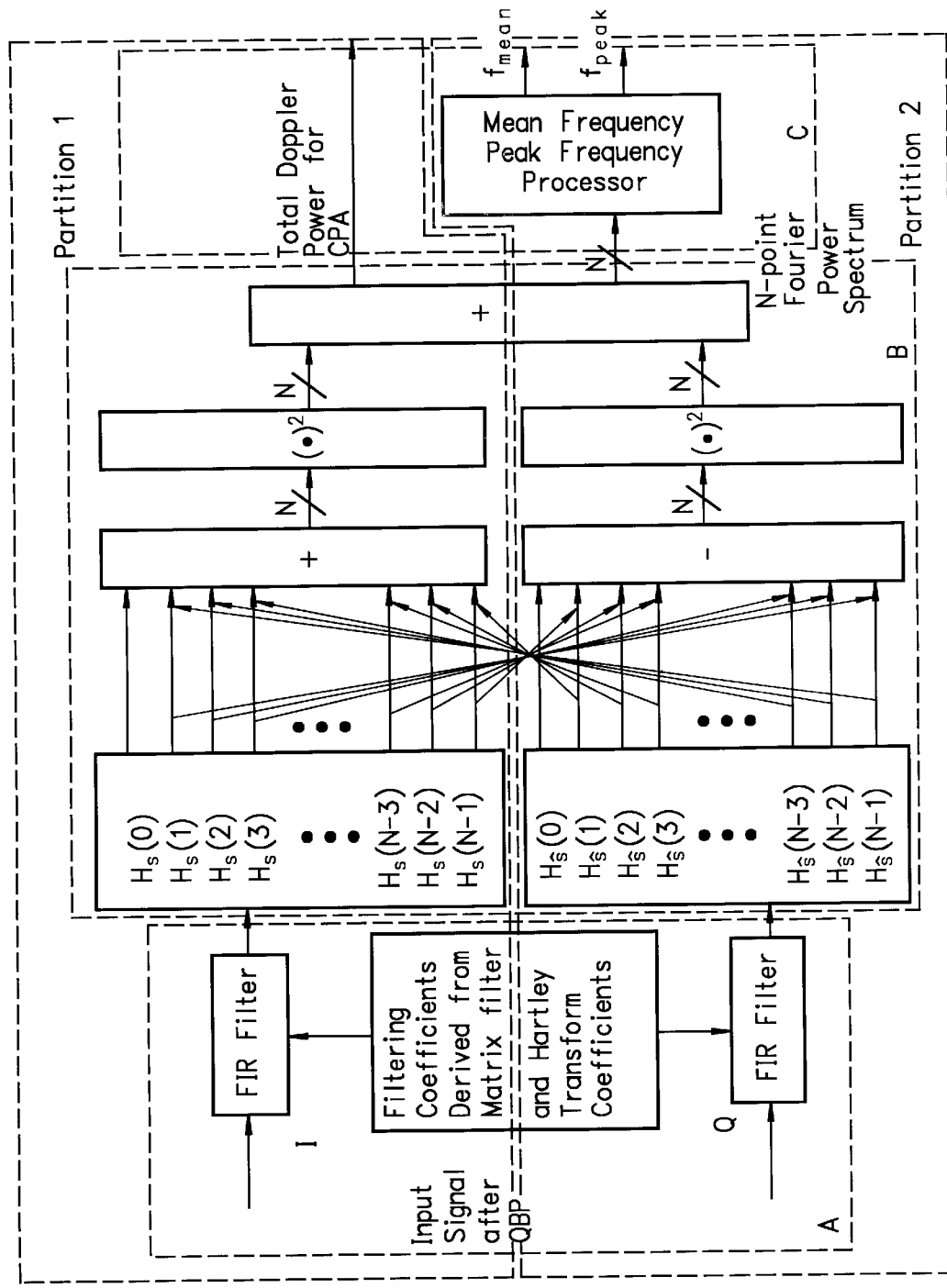
FIG. 9 is a processing block diagram for computing Fourier power spectrum via a Hartley transform.

FIG. 9 shows the processing architecture for computing the Fourier power spectrum based on Hartley transform. Notice the processing in block A is the matrix filtering except the filtering coefficients are modified according to the Hartley transform. Block B is the circuit to convert the output of the Hartley transform to obtain the Fourier power spectrum. Block C is a processor to compute the mean frequency or the peak frequency from the Fourier power spectrum. Let the filtering matrix be $M_{eh}$ which can be represented by $$M_{eh} = \begin{bmatrix} \overset{\perp}{\beta}_0^T, \overset{\perp}{\beta}_1^T, \overset{\perp}{\beta}_2^T, \ldots, \overset{\perp}{\beta}_{N-2}^T, \overset{\perp}{\beta}_{N-1}^T \end{bmatrix}$$

where $\overset{\perp}{\beta}_j^T$ is the jth row vector that consists of the filtering coefficients of the filtering matrix $M_{eh}$.

Thus, if one calculate $H_s(j) = \overset{\perp}{\beta}_j^T \cdot s(j) = \overset{\perp}{\beta}_{N-j}^T \cdot \hat{s}(N-j)$ simultaneously, that is, filtering the I signal and the time-reversed Q signal with filtering coefficient vector $\overset{\perp}{\beta}_j^T$ and $\overset{\perp}{\beta}_{N-j}^T$ respectively, the power spectrum $$P_z(j) = (H_s(j) \cdot H_s(N-j))^2 + (H_s(j) - H_s(N=j))^2$$

can be computed synchronously.

The computation required for the wall filtering process is $N^2$ multiplication and N(N-1) addition. The computation required for computing the power spectrum is 2N multiplication and 2N-2 additions. Thus, the hardware required for calculating the Fourier power spectrum is about a factor of N/2 less than the wall filtering process.

As shown in FIG. 9, if the signal processing is partitioned into two single channel processing modules, the only differences between partition 1 and partition 2 is in block C. In partition 1, C is used for Doppler power calculation whereas in partition 2, C is used for mean frequency calculation. Thus, for a low cost product in which only single channel processing is used for Doppler power computation, only half of the processing is required. If single channel module is implemented into ASIC to support CPA such as in Cozumel, one may also support color flow by simply adding an additional channel.

Figure 10A:
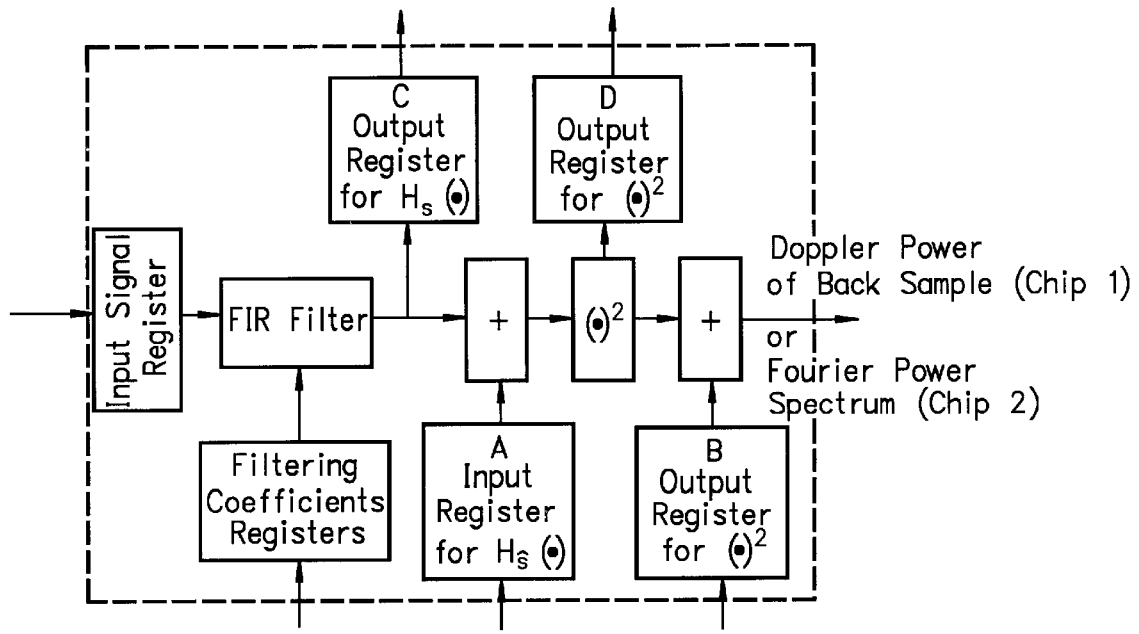
FIGS. 10(a), 10(b), and 10(c) illustrate a single channel processing chip, a multiply accumulator in the chip, and the use of two chips to obtain both mean frequency and Doppler power simultaneously, respectively.
Figure 10B:
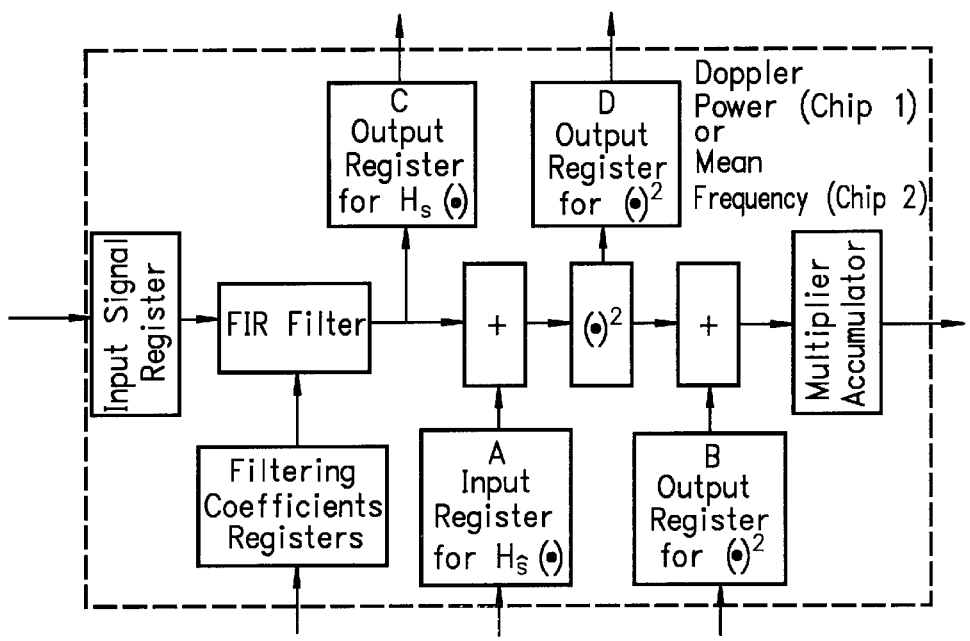
Figure 10C:
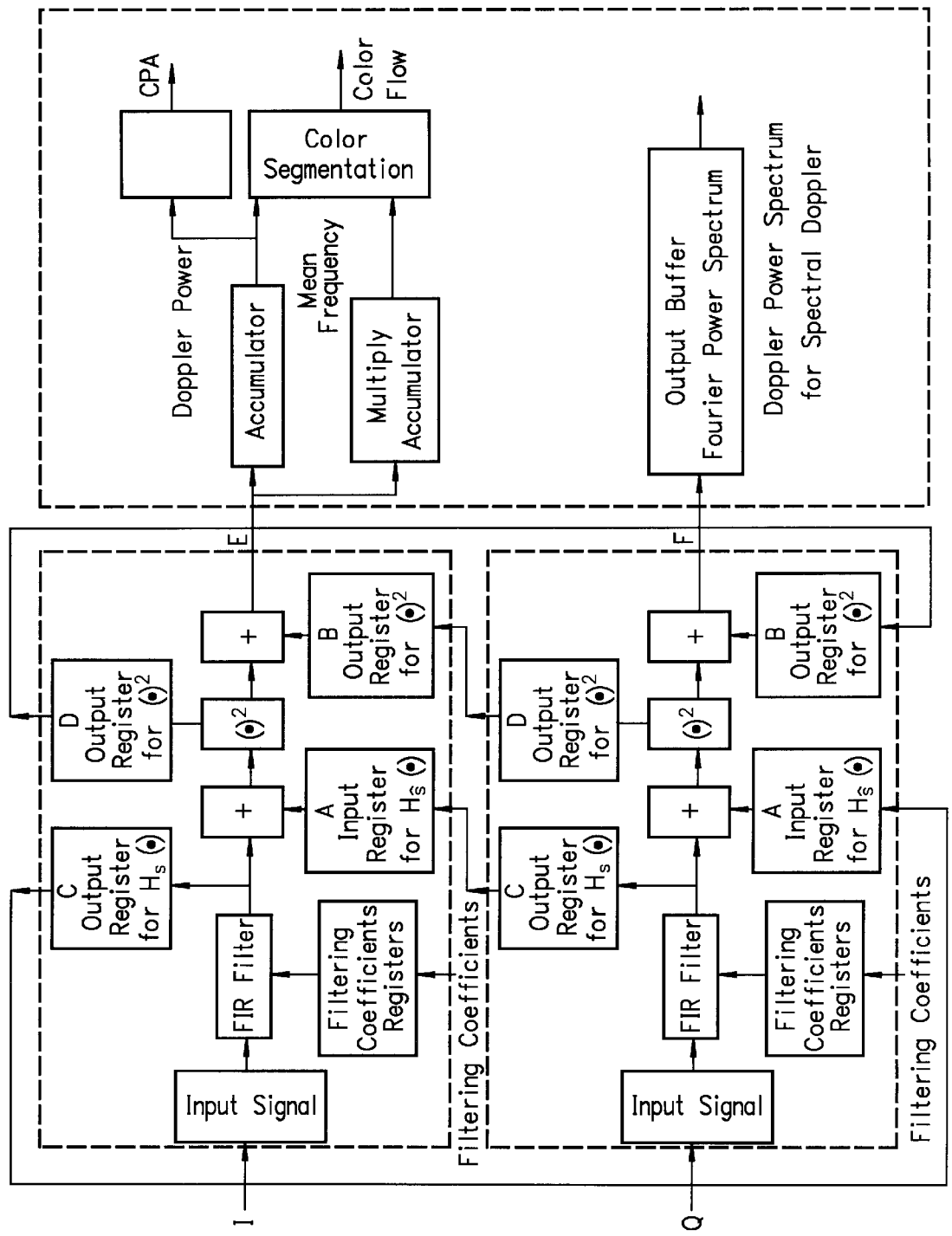

Two possible single channel partitions for signal processing are shown in FIGS. 10(a) and 10(b). In FIG. 10(a), registers A, B, C, and D are used for receiving values of $H_s(\bullet)$ and $(H_s(\bullet)-H_s(\bullet))^2$ from the second channel, sending values of $H_s(\bullet)$ and $(H_s(\bullet)+H_s(\bullet))^2$ to the second channel. By loading the typical matrix filtering coefficient and setting registers A, B, C, D to Zero, the output of single channel is the Doppler power of each sample in an ensemble. An accumulator can be used to integrate the Doppler power in an ensemble in single channel processing. For quadrature channels, two chips can be used as shown in FIG. 10(c). By modifying the filtering coefficients in both channels according to Equations (5) and (6) and clocking the values from registers C and D of one channel to registers A and B of the other channel, the output E and F in both chips are the Fourier power spectrum. One may use the processor off-chip to obtain Doppler power spectrum for spectral Doppler, CPA and color flow imaging.

If a multiply accumulator is also designed inside the chip as shown in FIG. 10(b), then both average Doppler power and mean frequency are available from dual chip processing. However, in a low-cost system when only CPA is needed, the cost is slightly higher as a result of inclusion of multiply accumulator when only accumulator is needed for Doppler power computation.

Attached hereto and incorporated herewith is another description of the signal processing algorithm and the application thereof in directional Power Doppler imaging applications.

For 2D echo imaging, wall filtering is not needed. The FIR filter may also be used for higher order filtering. The processor may also be used to obtain short term Fourier spectrum for tissue characterization. It can also be used to calculate DCT for data compression. For frequency compounding, the echo signal can be summed after filtering is detected.

The back end and ASIC 50 is the location of the RISC processor 502, which is used to coordinate the timing of all of the operations of the handheld ultrasound system. The RISC processor is connected to all other major functional areas of the ASICs to coordinate process timing and to load buffers and registers with the data necessary to perform the type of processing and display desired by the user. Program data for operation of the RISC processor is stored in a program memory 52 which is accessed by the RISC processor. Timing for the RISC processor is provided by clock signals from the clock generator located on the front end ASIC 30. The RISC processor also communicates through a PCMCIA and/or infrared transmitter interface, by which the processor can access additional program data or transmit image information remotely. The interface can connect to a telemetry link or a modem for the transmission of ultrasound images from the handheld unit to a remote location, for instance.

The RISC processor is operated under user control by commands and entries made by the user on the user control 70. A chart showing control functions, the type of controls, and their description is shown in FIG. 8. It will be appreciated that a number of functions, such as patient data entry, Cineloop operation, and 3D review, will operate through menu control to minimize the number of key or button controls on the small handheld unit. To further simplify the unit a number of operating functions are preprogrammed to specific diagnostic applications and will operate automatically when a specific application is selected. Selection of B mode imaging will automatically invoke frequency compounding and depth dependent filtering on the digital signal processing ASIC 40, for instance, while a four multiplier filter will automatically be set up as a wall filter on the DSP ASIC when Doppler operation is selected. The menu selection of specific clinical applications can automatically invoke specific feature settings such as TGC control characteristics and focal zones, for example.

While the invention has been described with reference to specific embodiments, the description is illustrative of the invention and is not to be construed as limiting the invention. Various modifications and applications may occur to those skilled in the art without departing from the true scope and spirit of the invention as defined by the appended claims.

What is claimed is:

1. In an ultrasound device, a digital signal processor comprising:
   a digital B mode filter for filtering B mode signals;
   a digital Doppler filter for filtering Doppler signals including wall filtering and Hartley transform matrix functions to obtain a Fourier power spectrum,
   a B mode signal detection and mapping circuit; and
   a Doppler signal estimator circuit using the Fourier power spectrum.

2. The digital signal processor of claim 1, wherein said digital filters, said B mode signal detection and mapping circuit, and said Doppler signal estimator circuit are located on a digital signal processing integrated circuit chip.

3. The digital signal processor of claim 1, wherein common elements of said digital signal processor are used for Doppler processing of Doppler signals, and also for B mode processing of B mode signals.

4. The digital signal processor of claim 3, wherein said common elements include elements of said digital filter circuits.

5. The digital signal processor of claim 4, wherein said digital signal processor includes a digital filter which is operated as a bandpass filter for B mode signals, and as a high pass filter for Doppler signals.

6. The digital signal processor of claim 4, wherein said digital signal processor includes a digital filter which is operated as a bandpass filter for B mode signals and as a wall filter for Doppler signals.

7. The digital signal processor of claim 1, wherein said digital signal processor further includes a normalization circuit for normalizing variations in the transducer aperture.

8. The digital signal processor of claim 1, wherein said digital signal processor further includes means for forming a synthetic aperture.

9. The digital signal processor of claim 1, wherein said digital signal processor further includes a depth dependent filter.

10. The digital signal processor of claim 1, wherein said digital signal processor further includes a speckle reduction circuit.

11. The digital signal processor of claim 1, wherein said digital signal processor further includes a flash suppression circuit for Doppler signals.

12. The digital signal processor of claim 1, wherein said digital signal processor further includes means for assembling scanlines from multiple focal zones.

13. The digital signal processor as defined by claim 1 wherein the Hartley transform matrix functions are implemented in two matrices for in-phase and quadrature signals.

14. The digital signal processor as defined by claim 1 wherein said processor comprises an application specific integrated circuit.

15. The digital signal processor as defined by claim 1 wherein flow direction and power are calculated simultaneously.

16. The digital signal processor as defined by claim 1 wherein directional Doppler information is computed via matrix filtering.

17. The digital signal processor as defined by claim 16 wherein directional Doppler information is displayed without temporal frame averaging.

18. The digital signal processor as defined by claim 16 wherein power Doppler information is displayed without temporal frame averaging.

19. The digital signal processor as defined by claim 1 wherein power Doppler information is computed via matrix filtering.

20. In an ultrasound device, a digital signal processor comprising:
   a digital B mode filter for filtering B mode signals;
   a digital Doppler filter for filtering Doppler signals including wall filtering and Hartley transform matrix functions to obtain a Fourier power spectrum,
   a B mode signal detection and mapping circuit;
   a Doppler signal estimator circuit using the Fourier power spectrum,
   wherein power Doppler information is computed in cardiac applications via matrix filtering without temporal frame averaging.

21. In an ultrasound device, a digital signal processor comprising:
   a digital B mode filter for filtering B mode signals;
   a digital Doppler filter for filtering Doppler signals including wall filtering and Hartley transform matrix functions to obtain a Fourier power spectrum, wherein the Hartley transform matrix functions are implemented in two matrices for in-phase and quadrature signals, the output from the in-phase matrix is operated on by a processing unit to provide total Doppler power and the output from the quadrature matrix is operated on by a processing unit to obtain mean frequency and peak frequency from the Fourier power spectrum;
   a B mode signal detection and mapping circuit; and
   a Doppler signal estimator circuit using the Fourier power spectrum.

22. The digital signal processor as defined by claim 21 wherein each matrix is implemented by passing an input signal sample through a FIR filter to summing and multiplication stages with registers connected thereto for receiving processed values and producing the Doppler power of each sample.

23. The digital signal processor as defined by claim 22 wherein filtering coefficients are defined according to:

$$\overset{\scriptscriptstyle\vee}{H} = M_h \overset{r}{y} = M_h M_f \overset{r}{z} = M_h M_f \left( \overset{r}{s} + j\overset{\perp}{s} \right) = M_{eh}\left( \overset{r}{s} + j\overset{\perp}{s} \right)$$

where the Discrete Hartley Transformation matrix is $M_h$, the Hartley transformation of the analytic signal $\overset{r}{z}$ is $\overset{\scriptscriptstyle\vee}{H}$, and $$M_{eh} = M_h M_f.$$

24. The digital signal processor as defined by claim 23 wherein the digital Doppler filter further includes an accumulator for providing Doppler power for use in color power Doppler and a multiply accumulator for providing mean frequency for use in color flow.

25. The digital signal processor of claim 24 wherein flow direction and power are calculated simultaneously.

26. The digital signal processor as defined by claim 25 wherein said processor comprises an application specific integrated circuit.

27. The digital signal processor as defined by claim 25 wherein display of directional power Doppler information requires no temporal frame averaging.

28. The digital signal processor as defined by claim 25 wherein display of power Doppler information is computed by matrix filtering with no temporal frame averaging.

29. A digital signal processor for a hand-held ultrasonic device comprising:

a digital B mode filter for filtering B mode signals;

a digital Doppler filter for filtering Doppler signals including wall filtering and Hartley transform matrix functions to obtain a Fourier power spectrum, a B mode signal detection and mapping circuit; and a Doppler signal estimator circuit using the Fourier power spectrum.

30. The digital signal processor of claim 29, wherein said digital filters, said B mode signal detection and mapping circuit, and said Doppler signal estimator circuit are located on a digital signal processing integrated circuit chip.

31. The digital signal processor of claim 29, wherein common elements of said digital signal processor are used for Doppler processing of Doppler signals, and also for B mode processing of B mode signals.

32. The digital signal processor of claim 31, wherein said common elements include elements of said digital filter circuits.

33. The digital signal processor of claim 32, wherein said digital signal processor includes a digital filter which is operated as a bandpass filter for B mode signals, and as a high pass filter for Doppler signals.

34. The digital signal processor of claim 32, wherein said digital signal processor includes a digital filter which is operated as a bandpass filter for B mode signals and as a wall filter for Doppler signals.

35. The digital signal processor of claim 29, wherein said digital signal processor further includes a normalization circuit for normalizing variations in the transducer aperture.

36. The digital signal processor of claim 29, wherein said digital signal processor further includes means for forming a synthetic aperture.

37. The digital signal processor of claim 29, wherein said digital signal processor further includes a depth dependent filter.

38. The digital signal processor of claim 29, wherein said digital signal processor further includes a speckle reduction circuit.

39. The digital signal processor of claim 29, wherein said digital signal processor further includes a flash suppression circuit for Doppler signals.

40. The digital signal processor of claim 29, wherein said digital signal processor further includes means for assembling scanlines from multiple focal zones.

41. The digital signal processor as defined by claim 29, wherein the Hartley transform matrix functions are implemented in two matrices for in-phase and quadrature signals.

42. The digital signal processor as defined by claim 29, wherein said processor comprises an application specific integrated circuit.

43. The digital signal processor as defined by claim 29, wherein flow direction and power are calculated simultaneously.

44. The digital signal processor as defined by claim 29, wherein directional Doppler information is computed via matrix filtering.

45. The digital signal processor as defined by claim 44, wherein directional Doppler information is displayed without temporal frame averaging.

46. The digital signal processor as defined by claim 29, wherein power Doppler information is computed via matrix filtering.

47. The digital signal processor as defined by claim 44, wherein power Doppler information is displayed without temporal frame averaging.

* * * * *